(12) United States Patent
Thompson

(10) Patent No.: US 11,793,889 B2
(45) Date of Patent: Oct. 24, 2023

(54) METHODS FOR SELECTIVE KINASE INHIBITION BY ENDOGENOUSLY PRODUCED ANTAGONISTS OF ONE OR MORE KINASES

(71) Applicant: Kinase Pharma Inc., Calgary (CA)

(72) Inventor: Bradley G Thompson, Calgary (CA)

(73) Assignee: Kinase Pharma Inc., Calgary (CA)

( * ) Notice: Subject to any disclaimer, the term of this patent is extended or adjusted under 35 U.S.C. 154(b) by 726 days.

(21) Appl. No.: 16/139,835

(22) Filed: Sep. 24, 2018

(65) Prior Publication Data

US 2020/0093940 A1    Mar. 26, 2020

(51) Int. Cl.
*A61K 48/00*    (2006.01)
*A61P 35/00*    (2006.01)
*A61P 37/06*    (2006.01)

(52) U.S. Cl.
CPC ...... *A61K 48/0066* (2013.01); *A61K 48/0075* (2013.01); *A61K 48/0083* (2013.01); *A61P 35/00* (2018.01); *A61P 37/06* (2018.01)

(58) Field of Classification Search
CPC .. A61K 39/0011; A61K 48/00; A61K 48/005; A61K 2039/53; A61P 35/00; A61P 43/00; C12N 15/67; C12N 15/62; C12N 2310/3519; C12N 15/11; C12N 2501/165
See application file for complete search history.

(56) References Cited

U.S. PATENT DOCUMENTS

| | | |
|---|---|---|
| 7,169,901 B2 | 1/2007 | Baca et al. |
| 8,236,312 B2 * | 8/2012 | Park .................. A61P 35/00 424/142.1 |
| 8,557,238 B2 | 10/2013 | Ferrara et al. |
| 2015/0056190 A1 * | 2/2015 | Hegde .................. A61P 9/00 436/86 |
| 2019/0202911 A1 * | 7/2019 | Mukasa .................. A61K 45/06 |

FOREIGN PATENT DOCUMENTS

WO PCT/US2016/058093 A1    4/2017

OTHER PUBLICATIONS

Hu et al., Four-in-one antibodies have superior cancer inhibitory activity against EGFR, HER2, HER3, and VEGF through disruption of HER/MET crosstalk, Cancer Research, vol. 75, pp. 159-170. (Year: 2015).*

Dekaris et al., Three-year corneal graft survival rate in high-risk cases treated with subconjunctival and topical bevacizumab, Graefe's Archives for Clinical and Experimental Ophthalmology, vol. 253, pp. 287-294. (Year: 2015).*

MacMillan et al., Bevacizumab diminishes experimental autoimmune encephalomyelitis by inhibiting spinal cord angiogenesis and reducing peripheral T-cell responses, Journal of Neuropathology and Experimental Neurology, vol. 71, pp. 983-999. (Year: 2012).*

Bhullar et al., "Kinase-targeted Cancer Therapies: Progress, Challenges and Future Directions", Molecular Cancer, 2018 17:48:1-20.

International Search Report and Written Opinion of PCT/CA2019/051349 dated Nov. 20, 2019.

Jahanban-Esfahlan et al., "The herbal medicine Melissa officinalis extract effects on gene expression of p53, Bcl-2, Her2, VEGF-A and hTERT in human lung, reast and prostate cancer cell lines". Gene, Mar. 1, 2017 (Mar. 1, 2017), vol. 613, pp. 14-19, (abstract).

Bancroft et al., "Effects of pharmacologic antagonists of epidermal growth factor receptor, P13K and MEK signal kinases on NF-KB and AP-1 activation an IL-8 and VEGF expression in human head and neck squamous cell carcinoma lines". Int. J. Cancer, 2002, vol. 99, pp. 543-548, (abstract).

Faltus et al., "Silencing of the HER2/neu Gene by siRNA Inhibits Proliferation and Induces Apoptosis in HER2/neu-Overexpressing Breast Cancer Cells". Neoplasia, Nov./Dec. 2004 (Nov./Dec. 2004), vol. 6 (6), pp. 786-795, (abstract, Introduction).

Walters et al., "Inhibition of the Growth of Patient-Derived Pancreatic Cancer Xenografts with MEK Inhibitor Trametinib Is Augmented by Combined Treatment with the Epidermal Growth Factor Receptor/HER2 Inhibitor Lapatinib". Neoplasia, Feb. 2013 (Feb. 2013), vol. 15 (2), pp. 143-155.

\* cited by examiner

*Primary Examiner* — Dana H Shin
(74) *Attorney, Agent, or Firm* — Gowling WLG (Canada) LLP

(57) ABSTRACT

The present disclosure relates to one or more agents, therapies, treatments, and methods of use of the agents and/or therapies and/or treatments for selectively inhibiting one or more kinases in one or more tissues. Embodiments of the present disclosure can be used as a therapy or a treatment for a subject where the selective inhibition of kinases with endogenously produced antagonists of kinases may be useful in treating conditions such as cancer, autoimmune disease, and transplant rejection.

4 Claims, No Drawings
Specification includes a Sequence Listing.

SEQUENCE LISTING

```
<160> NUMBER OF SEQ ID NOS: 6

<210> SEQ ID NO 1
<211> LENGTH: 372
<212> TYPE: DNA
<213> ORGANISM: Artificial Sequence
<220> FEATURE:
<223> OTHER INFORMATION: Synthetic Sequence

<400> SEQUENCE: 1
gaagtacagc tcgttgaaag cggcggtgga ctggtgcagc caggggggtc tttgcgactg      60
tcttgtgccg catccggtta tacttttact aattatggaa tgaactgggt acggcaggcc    120
cctgggaagg gtctggaatg ggtaggttgg atcaatacct atacaggtga acctacctat    180
gctgccgact tcaaaaggcg gttcacattc agtctggata ctagcaaaag caccgcatac    240
ctccagatga actccctgcg cgcagaggac actgctgtgt actattgtgc caagtaccca    300
cactactacg gttcatccca ctggtatttc gatgtttggg gtcagggaac cctcgttaca    360
```

-continued

```
gttagtagtg cg                                                          372

<210> SEQ ID NO 2
<211> LENGTH: 324
<212> TYPE: DNA
<213> ORGANISM: Artificial Sequence
<220> FEATURE:
<223> OTHER INFORMATION: Synthetic Sequence

<400> SEQUENCE: 2
gatatacaga tgactcaatc tccttctagc ctgtccgcca gcgtggggga ccgagtgaca      60
atcacttgca gcgccagtca agatatttcc aattacttga attggtacca acagaagcct     120
ggaaaagcac ccaaggtgtt gatctacttt acctcttctc ttcattctgg tgtgccaagc     180
agattttctg gctctggtag tgggactgat ttcactctta ctatcagcag cttgcaacct     240
gaggatttcg caacctacta ttgtcaacag tattctactg tgccttggac atttggtcag     300
ggaactaagg tagaaatcaa acgc                                            324

<210> SEQ ID NO 3
<211> LENGTH: 360
<212> TYPE: DNA
<213> ORGANISM: Artificial Sequence
<220> FEATURE:
<223> OTHER INFORMATION: Synthetic Sequence

<400> SEQUENCE: 3
caggtacaac tgaaacaaag cgggcctggg ctggtccagc catcccaaag tttgtccata      60
acttgcactg ttagtggttt tagcttgacc aattacgggg tgcattgggt aagacagagt     120
cctggtaagg gcctcgaatg gctgggcgtg atatggtcag gcggcaatac tgactacaat     180
actccattta ccagcagatt gtccatcaat aaagataatt ctaaaagcca ggtattcttt     240
aagatgaact ctctgcagtc caatgatact gcaatttatt actgtgcccg agcacttacc     300
tactacgatt acgagttcgc atactggggc cagggtaccc tcgtgaccgt atctgcagcg     360

<210> SEQ ID NO 4
<211> LENGTH: 324
<212> TYPE: DNA
<213> ORGANISM: Artificial Sequence
<220> FEATURE:
<223> OTHER INFORMATION: Synthetic Sequence

<400> SEQUENCE: 4
gatatccttc tgactcaatc ccctgtgatt ctgtcagtgt caccagggga aagggtcagt      60
ttttcatgtc gcgcatctca aagcattggc actaacatcc actggtacca acaacgcaca     120
aacggaagtc cccgcttgct catcaagtat gcaagcgaat caatcagcgg gatcccttcc     180
aggttcagtg gtagtgggag tggtacagat ttcactctct caattaacag cgtagagtcc     240
gaggacatcg ccgactatta ttgccaacag aacaacaact ggcctactac atttggtgcc     300
ggtacaaaac tggagcttaa acgc                                            324

<210> SEQ ID NO 5
<211> LENGTH: 354
<212> TYPE: DNA
<213> ORGANISM: Artificial Sequence
<220> FEATURE:
<223> OTHER INFORMATION: Synthetic Sequence

<400> SEQUENCE: 5
caggtccaac tgcagcagcc tggggctgag cttgtgaagc ctggggcttc attgaagctg      60
```

```
tcctgcaagt cttccgggta caccttcacc agctactgga tgcactgggt gaggcagagg      120
cctggacatg gccttgagtg gatcggagag attgatcctt ctgacagtta taaagactac      180
aatcagaagt tcaaggacaa ggccacattg actgtggaca gatcctccaa cacagcctac      240
atgcacctca gcagcctgac atctgatgac tctgcggtct attattgtgc aagagcgatt      300
acgacgaccc cctttgactt ctggggccaa ggcaccactc tcacagtctc ctca            354

<210> SEQ ID NO 6
<211> LENGTH: 324
<212> TYPE: DNA
<213> ORGANISM: Artificial Sequence
<220> FEATURE:
<223> OTHER INFORMATION: Synthetic Sequence

<400> SEQUENCE: 6
gatattgtgc taactcagtc tccagccacc ctgtctgtga ctccaggaga tagcgtcagt       60
ctttcctgca gggccagcca gagtattagc aacaacctac actggtatca acaaaaatca      120
catgagtctc caaggcttct catcaagtat gcttcccagt ccatctctgg gatcccctcc      180
aggttcagtg gcagtggatc agggacagat ttcactctca gtatcaacag tgtggagact      240
gaagattttg gagtgtattt ctgtcaacag agtaacacct ggccgtacac gttcggaggg      300
gggaccaagc tggaaataaa acgg                                             324
```

METHODS FOR SELECTIVE KINASE INHIBITION BY ENDOGENOUSLY PRODUCED ANTAGONISTS OF ONE OR MORE KINASES

TECHNICAL FIELD

The present disclosure relates to agents, therapies, and methods of use of compounds, agents and/or therapies, for selective kinase-inhibition. In particular, embodiments of the present disclosure relate to the use of such agents, therapies and methods as a therapy or treatment for conditions resulting from the over, up, or mis-expression or activation of one or more kinase enzymes.

BACKGROUND

Conditions such as cancer, autoimmune disease, and transplant rejection are often the result of the over, up- or mis-regulation of specific kinase enzymes.

Known approaches for the inhibition of kinases with exogenous agents include treatment with small chemical entities and antibodies, which are commonly used to treat cancer, autoimmune disease, and transplant rejection.

Over 30 exogenously delivered kinase inhibitors have been approved by the United States Food and Drug Administration (Bhuller et al. (2018) Kinase-targeted cancer therapies: progress, challenges and future directions. Mol. Can. 17:48).

The selective inhibition of kinases with endogenously produced antagonists of kinases may be useful in treating conditions such as cancer, autoimmune disease, and transplant rejection.

SUMMARY

Some embodiments of the present disclosure relate to a method of making an agent/target cell complex. The method comprises a step of administering a therapeutically effective amount of the agent to a subject, wherein in some embodiments of the present disclosure the agent/target cell complex causes the down regulation of one or more genes that encode for the production and/or activation of one or more kinases in one or more tissues of the subject.

In some embodiments of the present disclosure at least two agents may be administered to a subject to form at least two different types of agent/target cell complexes and each type of agent/target cell complex causes a down regulation of one or more genes that encode for the production and/or activation of one or more kinases in one or more tissues of the subject.

In some embodiments of the present disclosure at least three agents may be administered to a subject to form at least three different types of agent/target cell complexes and each type of agent/target cell complex causes the down regulation of one or more genes that encode for the production and/or activation of one or more kinases in one or more tissues of the subject.

Some embodiments of the present disclosure relate to a method of making an agent/target cell complex, the method comprising a step of administering a sufficient amount of an agent to a target cell whereby the agent/target cell complex is formed. Wherein in some embodiments of the present disclosure the agent/target cell complex causes the down regulation of one or more genes that encode for the production and/or activation of one or more kinases in one or more tissues. In some embodiments of the present disclosure the agent/target cell complex causes the endogenous production of one or more regulatory molecules that causes the down regulation of one or more genes that encode for the production and/or activation of one or more kinases in one or more tissues. In some embodiments of the present disclosure the agent/target cell complex causes the endogenous production of both of the one or more antagonists and the one or more regulatory molecules that causes the down regulation of one or more genes that encode for the production and/or activation of one or more kinases.

Some embodiments of the present disclosure relate to a pharmaceutical composition that comprises an agent, a pharmaceutically acceptable carrier, and/or an excipient. In some embodiments of the present disclosure the agent causes the down regulation of one or more genes that encode for the production and/or activation of one or more kinases. In some embodiments of the present disclosure the agent causes the endogenous production of one or more regulatory molecules that causes the targeted down regulation of one or more genes that encode for the production and/or activation of one or more kinases. In some embodiments of the present disclosure the agent causes the endogenous production of both of the one or more antagonists and the one or more regulatory molecules that causes the down regulation of one or more genes that encode for the production and/or activation of one or more kinases in one or more tissues.

Some embodiments of the present disclosure relate to a kit used for treatment of a condition or for delivery of a therapy to a subject. The kit comprises a unit dosage of an agent, a carrier for the unit dosage, and instructions for administering the unit dosage to the subject. Wherein in some embodiments of the present disclosure the agent causes the down regulation of one or more genes that encode for the production and/or activation of one or more kinases in one or more tissues. Wherein in some embodiments of the present disclosure the agent causes the endogenous production of one or more regulatory molecules that causes the down regulation of one or more genes that encode for the production and/or activation of one or more kinases in one or more tissues. Wherein in some embodiments of the present disclosure the agent causes the endogenous production of both of the one or more antagonists and the one or more regulatory molecules that causes the down regulation of one or more genes that encode for the production and/or activation of one or more kinases in one or more tissues. The carrier may be a solid carrier, such as a pill or tablet, or a liquid. The instructions may describe how the solid carrier may be administered to a subject by various routes of administration for a desired effect. The instructions may also describe how the liquid carrier may be administered to a subject by various routes of administration for a desired effect.

Some embodiments of the present disclosure relate to a method of treating a condition. The method comprises a step of administering to a subject a therapeutically effective amount of an agent that may cause the down regulation of one, or some, or all of one or more genes in one or more tissues where those one or more genes encode for the production and/or activation of one or more kinases.

Some embodiments of the present disclosure relate to a method for causing the endogenous production of one, or some or all, of an antagonist of a kinase or a regulatory molecule that down regulates one or more genes that encode for the production and/or activation of one or more kinases in one or more tissues.

Some embodiments of the present disclosure relate to at least one approach for the down regulation of one or more genes that encode for the production and/or activation of one or more kinases in one or more tissues. A first approach utilizes one or more gene vectors that contain nucleotide sequences and/or genes that cause a subject that receives the one or more gene vectors to produce, or increase production of, one or more antagonists to cause the down regulation of one or more genes that encode for the production and/or activation of one or more kinases in one or more tissues. Another approach utilizes one or more gene vectors that contain nucleotide sequences and/or genes that cause a subject that receives the one or more gene vectors to produce, or increase production of, one or more regulatory molecules that cause the down regulation of one or more genes that encode for the production and/or activation of one or more kinases in one or more tissues. Another approach utilizes one or more gene vectors that contain nucleotide sequences and/or genes that cause the subject that receives the one or more gene vectors to produce, or increase production of, the one or more antagonists and the one or more regulatory molecules.

Without being bound by any particular theory, therapies or treatments that comprise the use of antagonists or agonists of the targeted down-regulation a single gene encoding for a kinase, or the use of viral vectors that cause the targeted down regulation of a single gene encoding for a kinase, may be limited by the effectiveness of the treatment or therapy to access the subject's affected cells and/or tissues. Furthermore, the antagonists or agonists may impact only one of many genes found in the cell and/or tissues, which means that other genes that encode for the production and/or activation of one or more kinase may still influence the subject's condition.

Embodiments of the present disclosure may be useful for treating conditions such as cancer, autoimmune disease, and organ transplantation rejection, where the over, up, or mis-regulation of multiple genes that encode for kinases in one or more tissues may cause the condition.

DETAILED DESCRIPTION

Definitions

Unless defined otherwise, all technical and scientific terms used herein have the meanings that would be commonly understood by one of skill in the art in the context of the present description. Although any methods and materials similar or equivalent to those described herein can also be used in the practice or testing of the present disclosure, the preferred methods and materials are now described. All publications mentioned herein are incorporated herein by reference to disclose and describe the methods and/or materials in connection with which the publications are cited.

As used herein, the singular forms "a", "an", and "the" include plural references unless the context clearly dictates otherwise. For example, reference to "an agent" includes one or more agents and reference to "a subject" or "the subject" includes one or more subjects.

As used herein, the terms "about" or "approximately" refer to within about 25%, preferably within about 20%, preferably within about 15%, preferably within about 10%, preferably within about 5% of a given value or range. It is understood that such a variation is always included in any given value provided herein, whether or not it is specifically referred to.

As used here, the term "activity" is used interchangeably with "functionality" and both terms refer to the physiologic action of a biomolecule.

As used herein, the term "agent" refers to a substance that, when administered to a subject, causes one or more chemical reactions and/or one or more physical reactions and/or or one or more physiological reactions and/or one or more immunological reactions in the subject.

As used herein, the term "antagonist" refers to an agent that can, directly or indirectly, inhibit a physiologic activity and/or production of a target molecule within a subject that receives the agent.

As used herein, the term "ameliorate" refers to improve and/or to make better and/or to make more satisfactory.

As used herein, the term "biomolecule" refers to a carbohydrate, a protein, an amino acid sequence, a nucleic acid, a lipid, a primary metabolite, a secondary metabolite that is found within a subject. A biomolecule may be endogenous or exogenous.

As used herein, the term "cell" refers to a single cell as well as a plurality of cells or a population of the same cell type or different cell types. Administering an agent to a cell includes in vivo, in vitro and ex vivo administrations or combinations thereof.

As used herein, the term "complex" refers to an association, either direct or indirect, between one or more particles of an agent and one or more target cells. This association results in a change in the metabolism of the target cell. As used herein, the phrase "change in metabolism" refers to an increase or a decrease in the one or more target cells' production of deoxyribonucleic acid (DNA), ribonucleic acid (RNA), one or more proteins, or any post-translational modifications of one or more proteins.

As used herein, the term "effector molecule" refers to a molecule within a subject that can directly or indirectly regulate the metabolic activity of a target cell by increasing or decreasing the production of DNA, RNA, amino-acid sequences and/or by increasing or decreasing any post-translational modifications of one or more proteins.

As used herein, the term "endogenous" refers to the production, production and/or modification of a molecule that originates within a subject.

As used herein, the term "excipient" refers to any substance, not itself an agent, which may be used as a component within a pharmaceutical composition or a medicament for administration of a therapeutically effective amount of the agent to a subject. Additionally or alternatively an excipient may alone, or in combination with further chemical components, improve the handling and/or storage properties, and/or permit or facilitate formation of a dose unit, of the agent. Excipients include, but are not limited to, one or more of: a binder, a disintegrant, a diluent, a buffer, a taste enhancer, a solvent, a thickening agent, a gelling agent, a penetration enhancer, a solubilizing agent, a wetting agent, an antioxidant, a preservative, a surface active agent, a lubricant, an emollient, a substance that is added to mask or counteract a disagreeable odor, fragrances or taste, a substance that is added to improve appearance or texture of the composition and a substance used to form the pharmaceutical compositions or medicaments. Any such excipients can be used in any dosage forms according to the present disclosure. The foregoing classes of excipients are not meant to be exhaustive but are provided merely as illustrative of what a person of skill in the art would know and would also recognize that additional types and combinations of excipients may be used to achieve delivery of a therapeutically effective amount of the agent to a subject through one or more routes of administration.

As used herein, the term "exogenous" refers to a molecule that is within a subject but that did not originate within the subject.

As used herein, the terms "inhibit", "inhibiting", and "inhibition" refer to a decrease in activity, response, or other biological parameter of a biologic process, disease, disorder or symptom thereof. This can include but is not limited to the complete ablation of the activity, response, condition, or disease. This may also include, for example, a 10% reduction in the activity, response, condition, or disease as compared to the native or control level. Thus, the reduction can be a 10%, 20%, 30%, 40%, 50%, 60%, 70%, 80%, 90%, 100%, or any amount of reduction in between the specifically recited percentages, as compared to native or control levels.

As used herein, the term "medicament" refers to a medicine and/or pharmaceutical composition that comprises the agent and that can promote recovery from a disease, disorder or symptom thereof and/or that can prevent a disease, disorder or symptom thereof and/or that can inhibit the progression of a disease, disorder, or symptom thereof.

As used herein, the term "patient" refers to a subject that is afflicted with a disease. The term "patient" includes human and veterinary subjects.

As used herein, the term "pharmaceutical composition" means any composition for administration of an agent to a subject in need of therapy or treatment of a disease, disorder or symptom thereof. Pharmaceutical compositions may include additives such as pharmaceutically acceptable carriers, pharmaceutically accepted salts, excipients and the like. Pharmaceutical compositions may also additionally include one or more further active ingredients such as antimicrobial agents, anti-inflammatory agents, anaesthetics, analgesics, and the like.

As used herein, the term "pharmaceutically acceptable carrier" refers to an essentially chemically inert and non-toxic component within a pharmaceutical composition or medicament that does not inhibit the effectiveness and/or safety of the agent. Some examples of pharmaceutically acceptable carriers and their formulations are described in Remington (1995, The Science and Practice of Pharmacy (19th ed.) ed. A. R. Gennaro, Mack Publishing Company, Easton, PA), the disclosure of which is incorporated herein by reference. Typically, an appropriate amount of a pharmaceutically acceptable carrier is used in the formulation to render the formulation isotonic. Examples of suitable pharmaceutically acceptable carriers include, but are not limited to: saline solutions, glycerol solutions, ethanol, N-(1(2,3-dioleyloxy)propyl)-N,N,N-trimethylammonium chloride (DOTMA), diolesylphosphotidylethanolamine (DOPE), and liposomes. Such pharmaceutical compositions contain a therapeutically effective amount of the agent, together with a suitable amount of one or more pharmaceutically acceptable carriers and/or excipients so as to provide a form suitable for proper administration to the subject. The formulation should suit the route of administration. For example, oral administration may require enteric coatings to protect the agent from degrading within portions of the subject's gastrointestinal tract. In another example, injectable routes of administration may be administered in a liposomal formulation to facilitate transport throughout a subject's vascular system and to facilitate delivery across cell membranes of targeted intracellular sites.

As used herein, the phrases "prevention of" and "preventing" refer to avoiding an onset or progression of a disease, disorder, or a symptom thereof.

As used herein, the terms "production", "producing" and "produce" refer to the synthesis and/or replication of DNA, the transcription of one or more sequences of RNA, the translation of one or more amino acid sequences, the post-translational modifications of an amino acid sequence, the production of one or more regulatory molecules that can influence the production and/or functionality of an effector molecule or an effector cell. For clarity, "production" is also be used herein to refer to the functionality of a regulatory molecule, unless the context reasonably indicates otherwise.

As used herein, the terms "promote", "promotion", and "promoting" refer to an increase in an activity, response, condition, disease process, or other biological parameter. This can include but is not limited to the initiation of the activity, response, condition, or disease process. This may also include, for example, a 10% increase in the activity, response, condition, or disease as compared to the native or control level. Thus, the increase in an activity, response, condition, disease, or other biological parameter can be a 10%, 20%, 30%, 40%, 50%, 60%, 70%, 80%, 90%, 100%, or more, including any amount of increase in between the specifically recited percentages, as compared to native or control levels.

As used herein, the term "prophylactic administration" refers to the administration of any composition to a subject, in the absence of any symptom or indication of a disease or disorder, to prevent the occurrence of and/or the progression of the disease or disorder within the subject.

As used herein, the terms "signal molecule", "signalling molecule" and "regulatory molecule" can be used interchangeably and refer to a molecule that can directly or indirectly affect the production of an effector molecule or effector cell. Signal molecules can be enzymes or other types of biomolecules and they can act as a direct ligand on a target cell or they may influence the levels or functionality of a downstream ligand or receptor for a ligand.

As used herein, the term "subject" refers to any therapeutic target that receives the agent. The subject can be a vertebrate, for example, a mammal including a human. The term "subject" does not denote a particular age or sex. The term "subject" also refers to one or more cells of an organism, an in vitro culture of one or more tissue types, an in vitro culture of one or more cell types; ex vivo preparations; and a sample of biological materials such as tissue and/or biological fluids.

As used herein, the term "target cell" refers to one or more cells and/or cell types that are deleteriously affected, either directly or indirectly, by a disease.

As used herein, the term "therapeutically effective amount" refers to the amount of the agent used that is of sufficient quantity to ameliorate, treat and/or inhibit one or more of a disease, disorder or a symptom thereof. The "therapeutically effective amount" will vary depending on the agent used, the route of administration of the agent and the severity of the disease, disorder or symptom thereof. The subject's age, weight and genetic make-up may also influence the amount of the agent that will be a therapeutically effective amount.

As used herein, the terms "treat", "treatment" and "treating" refer to obtaining a desired pharmacologic and/or physiologic effect. The effect may be prophylactic in terms of completely or partially preventing an occurrence of a disease, disorder or symptom thereof and/or the effect may be therapeutic in providing a partial or complete amelioration or inhibition of a disease, disorder, or symptom thereof. Additionally, the term "treatment", refers to any treatment of a disease, disorder, or symptom thereof in a subject and includes: (a) preventing the disease from occurring in a subject which may be predisposed to the disease but has not yet been diagnosed as having it; (b) inhibiting the disease; and (c) ameliorating the disease.

As used herein, the terms "unit dosage form" and "unit dose" refer to a physically discrete unit that is suitable as a unitary dose for patients. Each unit contains a predetermined quantity of the agent and optionally, one or more suitable pharmaceutically acceptable carriers, one or more excipients, one or more additional active-ingredients, or combinations thereof. The amount of agent within each unit is a therapeutically effective amount.

In one embodiment of the present disclosure, the pharmaceutical compositions disclosed herein comprise an agent as described above in a total amount by weight of the composition of about 0.1% to about 2%. For example, the amount of the agent by weight of the pharmaceutical composition may be about 0.1%, about 0.2%, about 0.3%, about 0.4%, about 0.5%, about 0.6%, about 0.7%, about 0.8%, about 0.9%, about 1%, about 1.1%, about 1.2%, about 1.3%, about 1.4%, about 1.5%, about 1.6%, about 1.7%, about 1.8%, about 1.9%, or about 2%.

Where a range of values is provided herein, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges, and are also, encompassed within the disclosure, subject to any specifically excluded limit in the stated range. Where the stated range includes one or both of the limits, ranges excluding either or both of those included limits are also included in the disclosure.

The present disclosure relates to one or more agents, therapies, treatments, and methods of use of the agents and/or therapies and/or treatments that cause the inhibition of a kinase or kinases. Some embodiments of the present disclosure relate to methods for making a complex between at least one particle of an agent and at least one target cell of a subject where the complex causes the inhibition of a kinase or kinases in one or more tissues.

Embodiments of the present disclosure can be used as a therapy or a treatment for a patient.

In some embodiments of the present disclosure, the condition may be one that relates to an altered regulation of a kinase or kinases within the subject that has a condition, as compared to prior to the onset of the condition. Some non-limiting examples of the condition may include: cancer, autoimmune disease, and organ transplant rejection.

In some embodiments of the present disclosure, the agent can be administered to the subject by an intravenous route, an intramuscular route, an intraperitoneal route, an intrathecal route, an intravesical route, a topical route, an intranasal route, a transmucosal route, a pulmonary route, or combinations thereof.

In some embodiments of the present disclosure, the agent can be administered to the subject by pipetting a dose of the agent into an in vitro cell culture; perfusing or immersing an ex vivo cell or tissue preparation with a solution that comprises the agent; mixing a biological fluid sample with a solution or substrate that comprises the agent, or combinations thereof.

Some embodiments of the present disclosure relate to an agent that can be administered to a subject with the condition. When a therapeutically effective amount of the agent is administered to the subject, the agent may change or increase the inhibition of a kinase or kinases in one or more tissues of the subject.

For example, the agent may cause the inhibition of a kinase or kinases by changing the production of one or more sequences of DNA, one or more sequences of RNA and/or one or more proteins and/or one or more regulatory molecules that regulate the subject's levels and/or functionality of kinases and/or kinase effector molecules.

In some embodiments of the present disclosure, the subject may respond to receiving a therapeutically effective amount of the agent by changing production and/or functionality of one or more intermediary molecules by changing production of one or more DNA sequences, one or more RNA sequences, and/or one or more proteins that regulate the levels and/or functionality of the one or more intermediary molecules. The one or more intermediary molecules regulate the subject's levels and/or functionality of the one or more of the subject's levels and/or functionality of kinases and/or kinase effector molecules.

In some embodiments of the present disclosure, administering a therapeutic amount of the agent to a subject changes the production, functionality or both of one or more regulatory molecules that inhibits the production or functionality of one or more kinases. The one or more regulatory molecules can be a sequence of DNA, RNA or amino acids that inhibits the production and/or functionality of one or more one or more kinases after administration of the agent. The agent can increase the production and/or functionality of the one or more regulatory molecules by increasing one or more of: production of one or more nucleotides, nucleosides, sequences or genes that are related to causing increased amounts or functionality of the one or more regulatory molecules; transcription of RNA that is related to increased amounts or functionality of the one or more regulatory molecules; or translation of one or more amino acids or amino acid sequences that cause increased amounts or functionality of the one or more regulatory molecules.

In some embodiments of the present disclosure, the agent can be: a vector used for gene therapy; one or more selected nucleotides; a sequence of nucleotides; one or more nucleosides; a sequence of nucleosides; a DNA complex; one or more amino acids; a sequence of amino acids; a live microorganism; an attenuated microorganism; a dead microorganism; a recombinant virus; a non-recombinant virus; or combinations thereof.

In some embodiments of the present disclosure, the agent is a gene vector used for gene therapy. The gene therapy is useful for increasing the production of one or more antagonists that inhibit the production or functionality one or more kinases. Additionally or alternatively, the gene therapy is useful for inhibiting or for increasing the production of one or more regulatory molecules that inhibit the production or functionality one or more kinases.

In some embodiments of the present disclosure, the gene vector is a virus that can be within one or more of the following genus: flavivirus, influenza, enterovirus, rotavirus, rubellavirus, rubivirus, morbillivirus, orthopoxvirus, varicellovirus, dependoparvovirus, alphabaculovirus, betabaculovirus, deltabaculovirus, gammabaculovirus, mastadenovirus, simplexvirus, varicellovirus, cytomegalovirus, or combinations thereof. In some embodiments of the present disclosure the virus is an attenuated virus.

The embodiments of the present disclosure also relate to administering a therapeutically effective amount of the agent. The therapeutically effective amount of the agent will not substantially increase or cause any deleterious conditions within the subject. For example, the therapeutically effective amount will not cause cytokinesis, hypercytokinemia, or any other uncontrolled, or partially controlled, upregulation of the subject's immune system. In some embodiments of the present disclosure, the therapeutically effective amount of the agent that is administered to a patient is between about 10 and about $1\times10^{16}$ TCID$_{50}$/kg (50% tissue culture infective dose per kilogram of the patient's body weight). In some embodiments of the present disclosure the therapeutically effective amount of the agent that is administered to the patient is about $1\times10^{13}$ TCID$_{50}$/kg. In some embodiments of the present disclosure, the therapeutically effective amount of the agent that is administered to a patient is measured in TPC/kg (total particle count of the agent per kilogram of the patient's body weight). In some embodiments the therapeutically effective amount of the agent is between about 10 and about $1\times10^{16}$ TCP/kg.

Some embodiments of the present disclosure relate to a method for making an agent/target cell complex within a subject. The method comprises a step of administering a therapeutically effective amount of the agent to the subject. The complex comprises at least one particle of an agent and one or more target cells. When the complex is formed, it affects a change in metabolism of the one or more target cells that results in the subject downregulating the production and/or functionality of one or more kinases.

Some examples of a target cell that can form the agent/target cell complex include, but are not limited to: an adrenal gland cell; a B cell; a bile duct cell; a cancer cell, a chondrocyte; a cochlear cell; a corneal cell; a dendritic cell; an endocardium cell; an endometrial cell; an endothelial cell; an epithelial cell; an eosinophil; a fibroblast; a hair follicle cell; a hepatocyte; a lymph node cell; a macrophage; a mucosal cell; a myocyte; a neuron; a glomeruli cell; an optic nerve cell; an osteoblast; an ovarian tissue cell; a pancreatic islet beta cell; a pericardium cell; a platelet; a red blood cell (RBC); a retinal cell; a scleral cell; a Schwann cell; a stem cell, a T cell; a testicular tissue cell; a thyroid gland cell; a uveal cell; or combinations thereof.

Some embodiments of the present disclosure relate to a therapy that can be administered to a subject with one or more conditions that are related to, directly or indirectly, an altered regulation of two or more genes within the subject. The therapy comprises a step of administering to the subject a therapeutically effective amount of an agent that will: decrease production and/or activity of one or more regulatory molecules that increase the production and/or activity of one or more kinases; decrease production and/or activity of one or more kinases; or increase the production and/or activity of one or more regulatory molecules that decrease the production and/or activity of one or more kinases. When the therapy is administered to a patient, the therapy may change the in vivo production and/or functionality of one or more regulatory molecules and/or decrease the production and/or functionality of the one or more kinases. The decreased production and/or functionality of the kinases may reduce or remove the deleterious effects of the condition upon the patient.

Some embodiments of the present disclosure relate to a method of treating a condition where the method comprises a step of administering to the subject a therapeutically effective amount of an agent that will: decrease production and/or activity of one or more regulatory molecules that increase the production and/or activity of one or more kinases; decrease production and/or activity of one or more kinases; or increase the production and/or activity of one or more regulatory molecules that decrease the production and/or activity of one or more kinases.

Some embodiments of the present disclosure relate to therapies, treatments, and methods of use of more than one agent for regulation of two or more kinase genes in one or more tissues.

In some embodiments of the present disclosure, the first agent, the second agent, the third agent and the another agent and/or further agents can each increase or decrease the production and/or functionality of a regulatory molecule that, directly or indirectly, inhibits the production and/or functionality of a kinase or kinases.

EXAMPLES

Some examples of regulatory molecules that are involved in regulation of phosphorylation include: enzymes such as HER2, Braf, Jak 1/2/3, VEGF, EGFR, Flt3, BTK, ALK, and MEK.

In one example, the agent is an AAV6.2FF gene vector that includes a gene insert for the gene responsible for producing an anti-VEGF antibody in humans. In this example, the gene insert produces a biomolecule from the following base sequence for the variable heavy-chain of the anti-VEGF antibody (SEQ ID NO. 1):

```
gaagtacagctcgttgaaagcggcggtggactggtgcagccagggggtc
tttgcgactgtcttgtgccgcatccggttatacttttactaattatggaa
tgaactgggtacggcaggcccctgggaagggtctggaatgggtaggttgg
atcaatacctatacaggtgaacctacctatgctgccgacttcaaaaggcg
gttcacattcagtctggatactagcaaaagcaccgcatacctccagatga
actccctgcgcgcagaggacactgctgtgtactattgtgccaagtaccca
cactacacggttcatcccactggtatttcgatgtttggggtcagggaac
cctcgttacagttagtagtgcg
```

In another example, the agent is an AAV6.2FF gene vector that includes a gene insert for the gene responsible for producing an anti-VEGF antibody in humans. In this example, the gene insert produces a biomolecule from the following base sequence for the variable light-chain of the anti-VEGF antibody (SEQ ID NO. 2):

```
gatatacagatgactcaatctccttctagcctgtccgccagcgtggggga
ccgagtgacaatcacttgcagcgccagtcaagatatttccaattacttga
attggtaccaacagaagcctggaaaagcacccaaggtgttgatctacttt
acctcttctcttcattctggtgtgccaagcagattttctggctctggtag
tgggactgatttcactcttactatcagcagcttgcaacctgaggatttcg
caacctactattgtcaacagtattctactgtgccttggacatttggtcag
ggaactaaggtagaaatcaaacgc
```

In another example, the agent is an AAV6.2FF gene vector that includes a gene insert for the gene responsible for producing an anti-VEGF antibody in humans. In this example, the gene insert produces a biomolecule from the following base sequence for the variable heavy-chain of the anti-VEGF antibody (SEQ ID NO. 1) and the variable light-chain of the anti-VEGF antibody (SEQ ID NO. 2).

In another example, the agent is an AAV6.2FF gene vector that includes a gene insert for the gene responsible for producing an anti-EGFR antibody in humans. In this example, the gene insert produces a biomolecule from the following base sequence for the variable heavy-chain of the anti-EGFR antibody (SEQ ID NO. 3):

```
caggtacaactgaaacaaagcgggcctgggctggtccagccatcccaaag tttgtccataacttgcactgttagtggttttagcttgaccaattacgggg tgcattgggtaagacagagtcctggtaagggcctcgaatggctgggcgtg atatggtcaggcggcaatactgactacaatactccatttaccagcagatt gtccatcaataaagataattctaaaagccaggtattctttaagatgaact ctctgcagtccaatgatactgcaatttattactgtgcccgagcacttacc tactacgattacgagttcgcatactggggccagggtaccctcgtgaccgt atctgcagcg
```

In another example, the agent is an AAV6.2FF gene vector that includes a gene insert for the gene responsible for producing an anti-EGFR antibody in humans. In this example, the gene insert produces a biomolecule from the base sequence for the variable light-chain of the anti-EGFR antibody (SEQ ID NO. 4):

```
gatatccttctgactcaatccctgtgattctgtcagtgtcaccagggga aagggtcagtttttcatgtcgcgcatctcaaagcattggcactaacatcc actggtaccaacaacgcacaaacggaagtccccgcttgctcatcaagtat gcaagcgaatcaatcagcgggatccttccaggttcagtggtagtgggag tggtacagatttcactctctcaattaacagcgtagagtccgaggacatcg ccgactattattgccaacagaacaacaactggcctactacatttggtgcc ggtacaaaactggagcttaaacgc
```

In another example, the agent is an AAV6.2FF gene vector that includes a gene insert for the gene responsible for producing an anti-EGFR antibody in humans. In this example, the gene insert produces a biomolecule from the base sequence for the variable heavy-chain of the anti-EGFR antibody (SEQ ID NO. 3) and the variable light-chain of the anti-EGFR antibody (SEQ ID NO. 4).

In another example, the agent is an AAV6.2FF gene vector that includes a gene insert for the gene responsible for producing an anti-Flt-3 antibody in humans. In this example, the gene insert produces a biomolecule from the following base sequence for the variable heavy-chain of the anti-Flt-3 antibody (SEQ ID NO. 5):

```
caggtccaactgcagcagcctggggctgagcttgtgaagcctggggcttc attgaagctgtcctgcaagtcttccgggtacaccttcaccagctactgga tgcactgggtgaggcagaggcctggacatggccttgagtggatcggagag attgatccttctgacagttataaagactacaatcagaagttcaaggacaa ggccacattgactgtggacagatcctccaacacagcctacatgcacctca gcagcctgacatctgatgactctgcggtctattattgtgcaagagcgatt acgacgacccctttgacttctggggccaaggcaccactctcacagtctc ctca
```

In another example, the agent is an AAV6.2FF gene vector that includes a gene insert for the gene responsible for producing an anti-Flt-3 antibody in humans. In this example, the gene insert produces a biomolecule from the following base sequence for the base sequence for the variable light-chain of the anti-Flt-3 antibody (SEQ ID NO. 6):

```
gatattgtgctaactcagtctccagccaccctgtctgtgactccaggaga tagcgtcagtctttcctgcagggccagccagagtattagcaacaacctac actggtatcaacaaaaatcacatgagtctccaaggcttctcatcaagtat gcttcccagtccatctctgggatcccctccaggttcagtggcagtggatc agggacagatttcactctcagtatcaacagtgtggagactgaagattttg gagtgtatttctgtcaacagagtaacacctggccgtacacgttcggaggg gggaccaagctggaaataaaacgg
```

In another example, the agent is an AAV6.2FF gene vector that includes a gene insert for the gene responsible for producing an anti-Flt-3 antibody in humans. In this example, the gene insert produces a biomolecule from the following base sequence for the variable heavy-chain of the anti-Flt-3 antibody (SEQ ID NO. 5) and the variable light-chain of the anti-Flt-3 antibody (SEQ ID NO. 6).

The invention claimed is:

1. A method of treating one of cancer, autoimmune disease, and organ transplantation rejection, the method comprising a step of administering to a subject a therapeutically effective amount of an agent that downregulates a VEGF enzyme that is involved in regulation of phosphorylation, wherein the agent comprises a gene vector that comprises SEQ ID No. 1 and SEQ ID No. 2 for producing a regulatory molecule that downregulates the VEGF enzyme.

2. The method according to claim 1, wherein the step of administering occurs by at least one of an intravenous route, an intramuscular route, an intraperitoneal route, an intrathecal route, an intravesical route, a topical route, an intranasal route, a transmucosal route, and a pulmonary route.

3. The method according to claim 1, wherein the regulatory molecule that decreases production of the VEGF enzyme.

4. The method according to claim 1, wherein the regulatory molecule decreases activity of the VEGF enzyme.

* * * * *